United States Patent [19]

Ross

[11] Patent Number: Plant 7,046

[45] Date of Patent: Oct. 10, 1989

[54] HOSTA PLANT SOLAR FLARE

[76] Inventor: Henry A. Ross, 16711 Pearl Rd., Strongsville, Ohio 44136

[21] Appl. No.: 276,423

[22] Filed: Nov. 25, 1988

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A novel variety of Hosta, characterized by its large leaves of golden color borne on a large plant.

2 Drawing Sheets

BACKGROUND OF THE NEW VARIETY

The present invention relates to a new and distinct variety of Hosta plant; a clonal selection designated as Hosta 'Solar Flare'. This new Hosta displays a golden green leaf color in early Spring which changes to golden yellow, with bright green midrib and veins, as it matures. This plant is also easily distinguished by its unusually large size, when compared with other known Hosta plants.

About 20 years ago; when varieties of Hosta available were very limited; I began a program intended to develop superior, new varieties of Hosta in golden foliaged and variegated types. I began with open-pollinated seed collected from Hosta "Frances Williams", Hosta tokudama aureo-nebulosa and Hosta fortunei aurea. As the seedlings germinated, any which appeared to be golden-leaved or variegated were saved and planted out while the rest were discarded. Initially, out of many thousands of seedlings; only a few of the desired types appeared. Open pollinated seed was then collected from those which appeared to be most promising and again the selection process was repeated. In 1978; in third or fourth generation of open-pollinated seedlings; one appeared which was outstanding, unique and different from any others I had seen; here or anywhere else. This selection produced a huge plant with very large leaves which were of a most unique coloration; in that . . . as the season progressed . . . they developed into enormous light golden-yellow foliaged plants with a bright green midrib on the upper leaf surface; the green coloration also usually appearing in the veins on either side of the midrib as well. This CLONE was subsequently given the name of Hosta 'Solar Flare' and was registered with the American Hosta Society; (which is the International registrar for Hosta) in 1981 under the name of the Gardenview Horticultural Park of which I am the founder and director. Subsequently I propagated Hosta 'Solar Flare' vegetatively by natural division and now have about 8 clumps, all of which are absolutely identical with one another in all respects. The foliage of this clone begins with a greenish-gold in early Spring (more gold than green); and gradually changes, from week to week, until it matures at a light golden-yellow with bright green midrib and veins toward the end of the season. The nature and intensity of the yellow coloring depends upon light intensity and temperature. In shady, low light areas; it is greenish-gold while in full light it becomes a deep yellow and in full sun, it bleaches out to a very light yellow. The flowers are unimpressive and typical of hybrids of Hosta sieboldiana. Although registered in 1981;

this variety has never been released to the date of this application.

BRIEF DESCRIPTION OF THE DRAWINGS ATTACHED

The first sheet depicts a single-crown specimen of the claimed plant; centrally, within a plating of normal sized, sister seedling plants. The second sheet has two close-up views showing individual leaves having characteristic prominent, uniform veining. The upper drawing shows the coloring in full sun while the lower drawing shows the coloring in full light but minimum sun.

Color specifications are presented from Horticultural Colour Chart issued by the British Colour Council in collaboration with The Royal Horticultural Society (Wilson), except where ordinary terms of color are descriptive.

DESCRIPTION OF THE VARIETY

PLANT

A herbaceous, clump-forming plant with short rhozomes; forming a large clump with leaves basal, tufted, petioled. The plant is semi-upright in habit of growth and, under ideal growing conditions, easily reaches a foliage mass height of 3 feet with a comparable spread; depending upon whether it is a single crown plant or an old, established clump containing many crowns.

LEAVES

Made up of a leaf petiole up to 26" long, topped with an ovate leaf blade which; under ideal growing conditions; reaches up to 14" wide by 18 inches long. The leaf blade is ovate, base cordate with tip acute, margin entire and gently undulating, glaucous on top and pruniose beneath, with 18 pair of veins.

FOLIAGE COLORATION

Because the coloration varies; depending upon light conditions and temperature; it is not possible to assign any one specific color to the foliage. In low light, shady condition (in northern Ohio), the coloration is close to, but a bit deeper and more yellow than RHS Horticultural Color Chart Sap Green 62/3. In full light but no sun, the coloration is close to but a deeper, more muted shade of Barium Yellow 503/2. In full sun the coloration bleaches out to Straw Yellow (604/3). Towards the latter part of the season the upper midrib develops a bright green coloration which often also spreads to the veins as well. The attached color photographs depict the color variations as closely as it is possible to do so. The single photo shows a single-crown plant at midseason with the green midrib coloration beginning to appear. On page with the two photos; the upper photo shows the coloration in bright sun while the lower photo shows the coloration in full light but with no sun. Both photos were taken earlier in the season at which time the green veining had not yet appeared.

FLOWERS (*Not* a basis for this selection)

The flowers are unimpressive and typical of most Hosta sieboldiana x Hosta fortunei hybrids. The non-foliated flower stem is approximately 33 inches tall when the plant blooms and is then slightly above the developing foliage. As the foliage develops, it virtually hides the flower stem. Flowers funnelform up to 1½ inches long, almost white flushed with palest lilac, in a terminal, scapose, bracted, one-sided raceme, carrying 12–18 florets. Fertile.

This new and distinctive hybrid Hosta, of unknown parentage, was created by me. It is a *clonal* selection; which when vegetatively propagated, produces offspring all of which are absolutely identical with one another in all respects. The special characteristics upon which this selection was based are 1. The very large size of the plant
2. The very large size of the leaves
3. The unusual and distinctive coloration of the foliage.

This clonal selection is extremely vigorous in habit of plant growth and striking because of the size and unusual coloring of its foliage; especially toward the later part of the growing season when the green midrib and veining appear on the upper surface.

I claim:

1. A new and distinct variety of Hosta, substantially as described and illustrated; named Hosta 'Solar Flare'; particularly distinguished by its extreme large size and size of foliage in which the color ranges from golden-green to golden-yellow with bright green midrib and veins developing on the upper surface toward the end of the growing season.

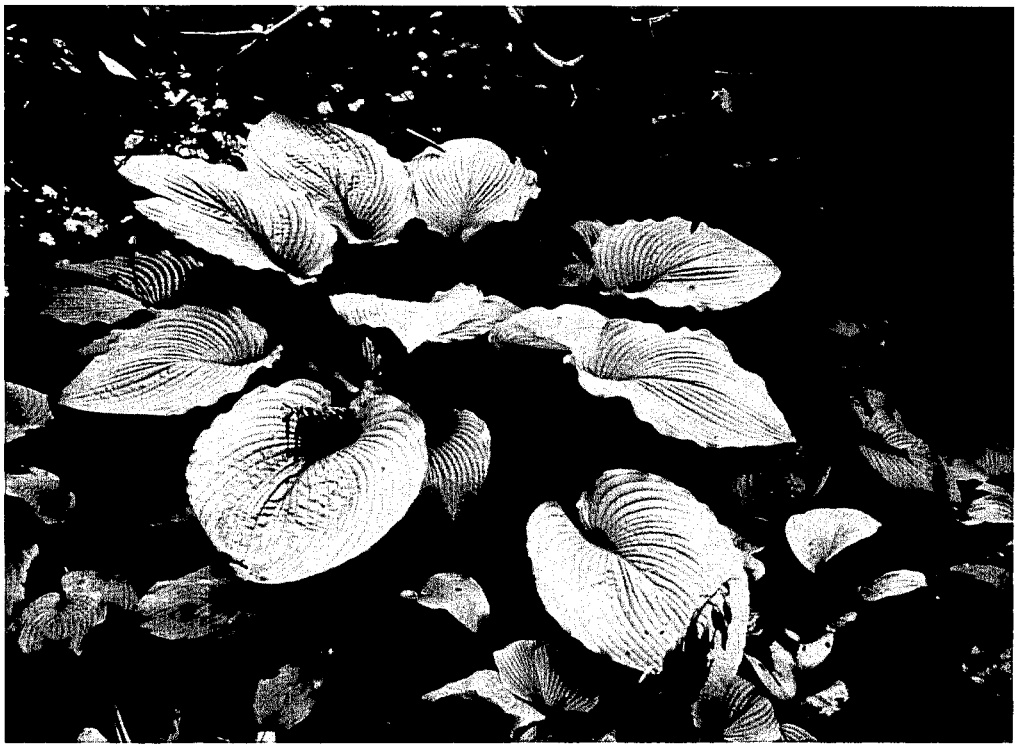

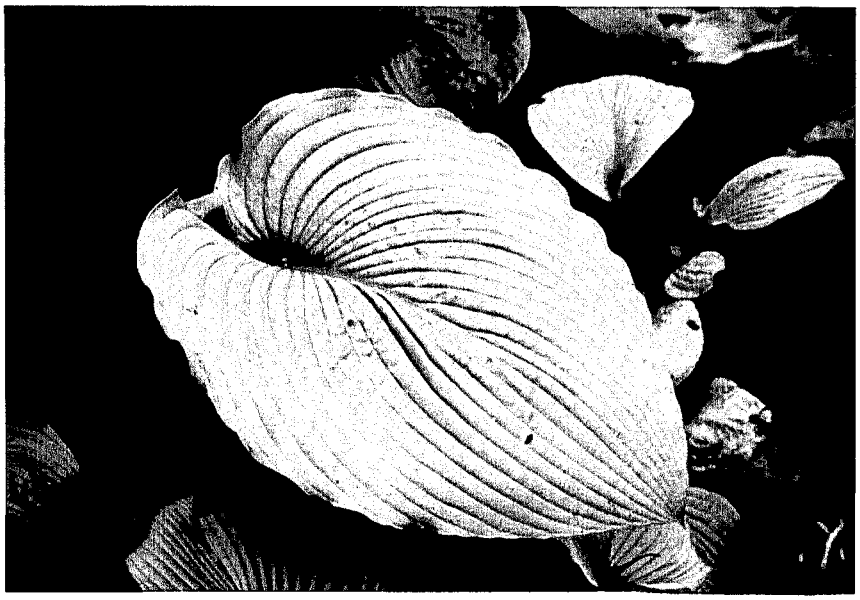
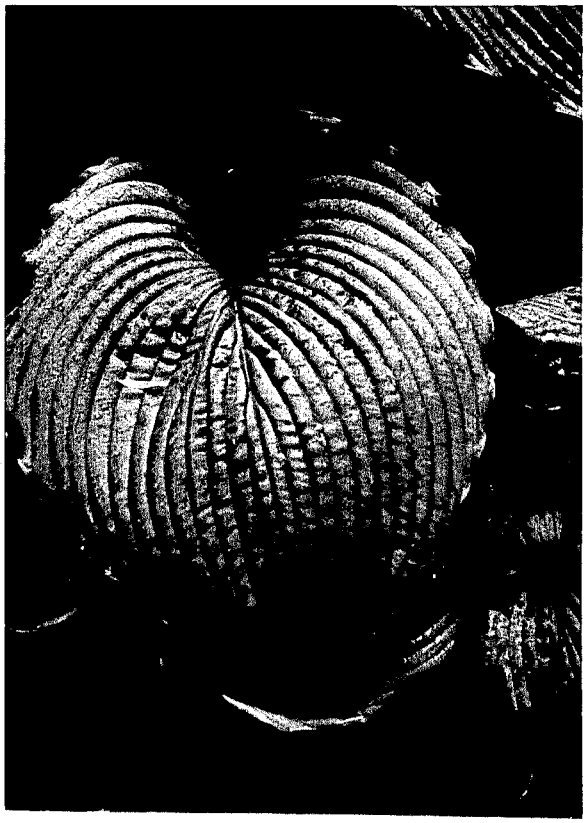

* * * * *